US006855152B2

(12) United States Patent
Suhm et al.

(10) Patent No.: US 6,855,152 B2
(45) Date of Patent: Feb. 15, 2005

(54) LASER POINTER

(75) Inventors: Norbert Suhm, Weil-Haltingen (DE); Peter Messmer, Oberwil (CH); Pietro Regazzoni, Basel (CH); Markus Hehli, Frauenkirch (CH); Paul Muller, Riehen (CH)

(73) Assignee: Synthes AG Chur, Chur (CH)

( * ) Notice: Subject to any disclaimer, the term of this patent is extended or adjusted under 35 U.S.C. 154(b) by 201 days.

(21) Appl. No.: 10/203,996

(22) PCT Filed: Dec. 18, 2000

(86) PCT No.: PCT/CH00/00668

§ 371 (c)(1),
(2), (4) Date: Aug. 15, 2002

(87) PCT Pub. No.: WO01/60259

PCT Pub. Date: Aug. 23, 2001

(65) Prior Publication Data
US 2003/0012342 A1 Jan. 16, 2003

(30) Foreign Application Priority Data

Feb. 15, 2000 (DE) ..................... 200 02 604 U

(51) Int. Cl.[7] .............................. A61B 19/00
(52) U.S. Cl. ................. 606/130; 378/206; 385/147; 430/945; 359/641; 33/227
(58) Field of Search .......................... 606/1, 130, 116; 604/116; 378/14, 145, 204, 206; 385/147; 430/945, 139, 198; 359/641; 33/227; 345/180–184; 128/920–925

(56) References Cited

U.S. PATENT DOCUMENTS

| 5,230,623 A | * | 7/1993 | Guthrie et al. ................. 433/72 |
| 5,279,309 A | * | 1/1994 | Taylor et al. ................. 600/595 |
| 5,537,453 A | | 7/1996 | Williams et al. |
| 5,661,775 A | | 8/1997 | Cramer et al. |
| 5,676,673 A | * | 10/1997 | Ferre et al. .................. 606/130 |
| 5,732,703 A | | 3/1998 | Kalfas et al. |
| 6,187,018 B1 | * | 2/2001 | Sanjay-Gopal et al. ...... 606/130 |
| 6,368,332 B1 | * | 4/2002 | Salcudean et al. .......... 606/130 |

* cited by examiner

Primary Examiner—Glenn K. Dawson
(74) Attorney, Agent, or Firm—Rankin, Hill, Porter & Clark LLP

(57) ABSTRACT

A device to be used in combination with a surgical navigation system for defining the position of a straight line determined by an operating surgeon within a three-dimensional coordinate system in an operating theater. The devices includes a body (1) with a surface (2) and at least three markers (3) which emit waves (19) and the position of which can be determined within a three-dimensional coordinate system by a position detector belonging to the surgical navigation system. A laser (4) mounted on the body (1) emits a laser beam (5), directed away from the body (1), which has a geometrical central beam (6) and a wavelength in the visible range. The laser beam (5) is emitted in a geometrically defined position relative to the markers (3) so that the position of the central beam (6) relative to the three-dimensional coordinate system can be calculated from the previously measured positions of the markers (3) by a computer, which is also part of the surgical navigation system.

21 Claims, 2 Drawing Sheets

LASER POINTER

Figure 1:
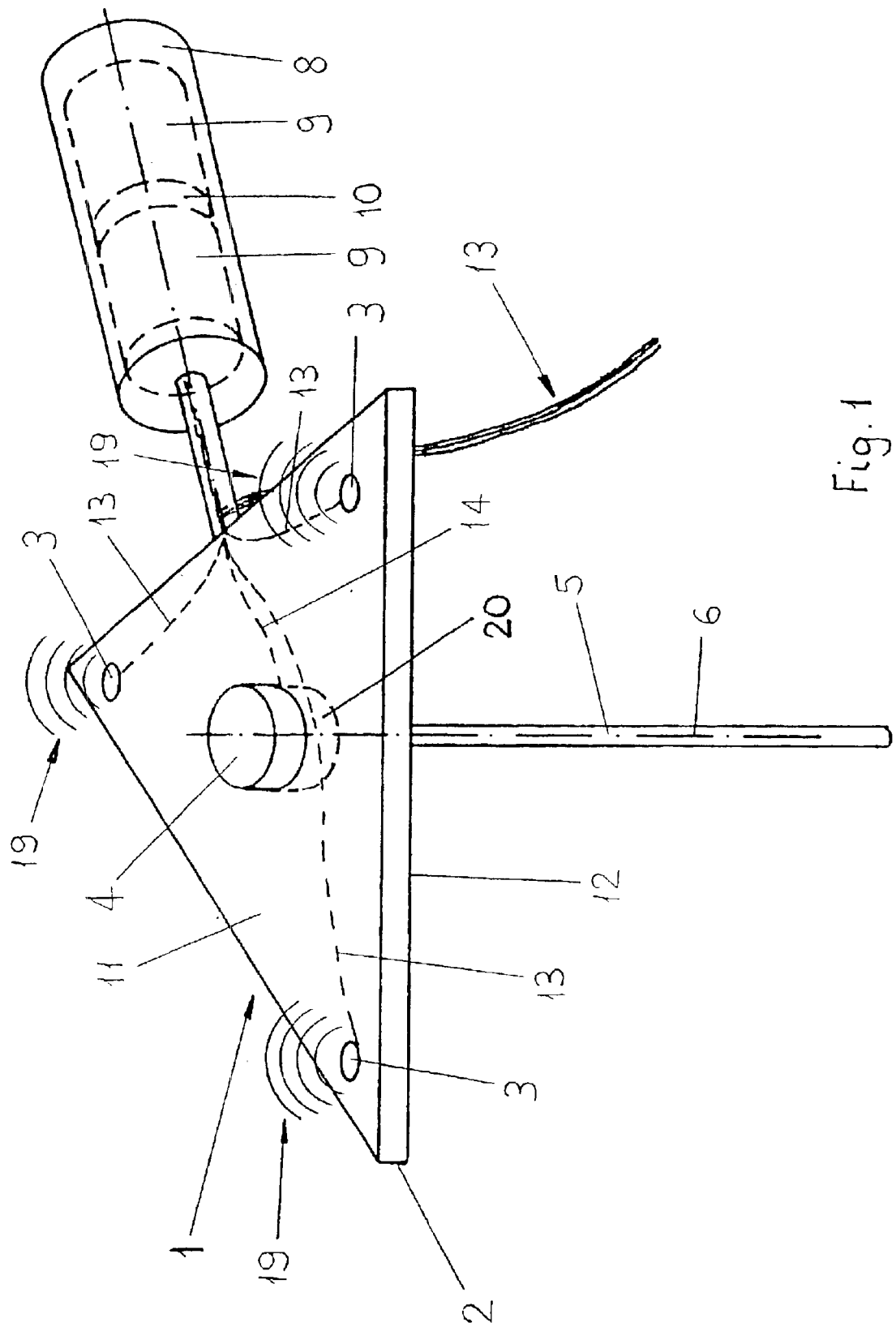

English translation of the International Patent Application No. PCT/CH00/00668 "Laser pointer" in the name of AO-Entwicklungsinstitut Davos

LASER POINTER

The invention relates to a device to be used in combination with a surgical navigation system for defining the position of a straight line determined by an operating surgeon within a three-dimensional coordinate system in an operating theatre as claimed in the precharacterising part of claim 1.

Increasingly, surgical navigation systems or devices known as Computer Assisted Surgery Systems (CAS) are used for the treatment of bone fractures in surgical operation theatres. With the aid of imaging techniques, these devices permit the utilisation of minimally invasive surgical procedures by enabling a position measuring of surgical instruments and devices within a three-dimensional coordinate system which is stationary relative to the operating theatre. This enables a computer-controlled displacement and positioning of devices such as medical robots or movable X-ray apparatuses, in particular those having an X-ray source mounted on one end of a three-dimensionally movable, C-shaped bow and an X-ray receiver mounted on the other end thereof (in the following briefly referred to as C-bow). A motor-driven and computer-controlled, movable C-bow of this type is disclosed in the international patent application PCT/CH00/00022.

Surgical navigation systems including a computer and a position detector for measuring the position of three-dimensionally movable, surgical instruments and devices are disclosed, for example, in U.S. Pat. No. 5,383,454 BUCHOLZ and in EP 0,359,773 SCHLÖNDORFF. Surgical navigation systems of this type are put on the market, for example, by the company MEDIVISION, Oberdorf, Switzerland, under the trade name "Surgigate". In addition to a computer provided with a data memory for storing X-ray photographs or entire computer tomograms (CTs) taken and stored prior to, or during the operation for diagnostic purposes or for planning the intervention to be carried out, these systems comprise at least one position detector. Frequently, optoelectronic position detectors are used which are capable of measuring the positions of optical markers applied to said surgical instruments or devices within a three-dimensional coordinate system in the operating theatre. Optoelectronic position detectors are commercially available, for example, under the trade name Optotrak 3020 (manufactured by Northern Digital, Ontario, Canada).

Usually, LEDs (light emitting diodes) or IREDs (infrared light-emitting diodes) are used as optical markers, the positions of which within a three-dimensional coordinate system are detectable by the sensor of the position detector, realised for example in the form of cameras or CCDs (charge-coupled devices).

Other position detectors may function on the basis of acoustic waves or magnetic fields, instead of electromagnetic waves.

In order to define an image plane or an image normal to be occupied by the C-bow, a pointer provided with markers, such as the one disclosed in U.S. Pat. No. 5,383,454 BUCHOLZ, may be positioned by the operating surgeon with its tip on the body of a patient while the shaft of the pointer is oriented in a selected direction corresponding to the image normal of the x-ray photograph to be taken. Pointers of this type are commercially available, for example, under the trade name Optotrak Digitizing Probes (manufactured by Northern Digital, Ontario, Canada). The positions of the markers fixed to the pointer are measured by the position detector and, based on these data, the position and orientation of the straight line defined by the longitudinal axis of the pointer within the three-dimensional coordinate system of the operating theatre is calculated by the computer. Subsequently, the C-bow may be displaced in a computer-controlled manner so as to occupy a position and projection the image normal of which corresponds to the longitudinal axis of the pointer. A disadvantage with the utilisation of such pointers resides in the fact that they are relatively short, which makes it necessary for the operating surgeon to approach the patient very closely when working with the pointer. In addition, the position of the image normal relative to the patient is not visualised with these known pointers, so that only inaccurate predictions of the resulting projection can be made. Due to the presence of the operating surgeon, the patient, and the C-bow, the visibility of the markers fixed on such small-sized pointers may be strongly limited for the navigation system and the markers may temporarily be even completely invisible.

The invention is intended to provide a remedy for this. It is accordingly an object of the invention to create a pointer embodied in such a way as to permit the operating surgeon to indicate the image normal or the projection plane from a greater distance. The greater spatial distances between the operating surgeon, the patient, and the surgical devices made possible by the invention permit an undisturbed detection of the markers by the sensors of the position detector. Thus it is possible, for example, to position a computer-controlled, motor-driven C-bow close to the patient without running the risk of a collision between the operating surgeon and the C-bow.

According to the invention, this object is achieved by means of a device to be used in combination with a surgical navigation system which shows the features of claim 1.

The inventive device to be used in combination with a surgical navigation system serves for defining the position of a straight line determined by the operating surgeon and of a plane extending vertically thereto within a three-dimensional coordinate system in an operating theatre. It comprises a body provided with at least three markers said markers emitting waves. A laser is integrated into said body in such a way that the laser beam, emitted concentrically to a central beam, is directed away from the body. The wave length of the laser beam is in the visible range, so that it is possible for the operating surgeon by directing the device and the laser beam adequately with respect to a patient to be treated so as to define a straight line in the operating theatre which intersects the patient and which corresponds, for example, to the image normal of a position and projection of a C-bow that is to be adjusted. The laser is fixed within the body in a defined position relative to the markers, so that the direction of the central beam is defined relative to the positions of the markers. The positions of the markers are measured by a position detector which is part of the surgical navigation system, so that the position of a straight line within a three-dimensional coordinate system in the operating theatre may be determined by means of a computer which is equally part of the surgical navigation system and the C-bow may be displaced to the desired position and projection in a computer-controlled manner.

In one embodiment, the device according to the invention comprises a handle which in the case of a battery-operated laser may be provided with a cavity for receiving the batteries.

The wattage of the laser is in a range of between 2 mw and 1 W, preferably between 2 mw and 25 mw.

The waves emitted by the markers are either electromagnetic or acoustic waves, depending on the type of position detector used. If markers emitting electromagnetic waves are used, the following embodiments of the markers are envisageable:

LEDs (light-emitting diodes);
IREDs (infrared light-emitting diodes);
optical reflectors; or
a fibre-optic light guide charged by a light source.

If markers emitting acoustic waves are used, the markers are embodied as acoustic emitters.

In one embodiment of the device according to the invention, the body is shaped in the form of a prismatic or cylindrical rod provided with a longitudinal axis. Preferably, the laser is integrated in the rod in such a way that the central beam coincides with the longitudinal axis of the rod and that the emitted laser beam is directed away from one of the rod ends. Three markers may be fixed in a non-collinear way to the rod or may be arranged on a straight line, preferably on the longitudinal axis, the three markers being arranged, in the latter case, at distances (A) or (B), respectively, relative to one another, with (A) being unequal to (B), so that it is possible to determine the direction of emission of the laser beam.

In another embodiment of the device according to the invention, the body is realised in the form of a planar plate, the markers being preferably arranged in a non-collinear way and emitting waves directed away from the surface of the plate. The laser is inserted substantially on centre in the plate, so that the laser beam emitted is directed away from the bottom surface of the plate.

Preferably, the markers are arranged in a plane extending parallel to the top surface, said plane and said top surface being likely to coincide and the laser beam is emitted vertically to said plane.

In a further embodiment of the device according to the invention, the laser comprises a system of lenses adapted to the wave length of the laser beam in order to allow the laser beam to be emitted in a geometrically defined position and direction relative to the positions of the markers. Instead of the system of lenses, a fibre-optic appliance, a system of optical reflectors or any other suitable beam deflection system may be used.

Further advantageous embodiments of the invention will be characterised in the dependent claims.

The advantages achieved by the present invention consist essentially in the fact that the device according to the invention makes it possible to define a straight line and a plane extending vertically thereto, relative to a patient in the operating theatre, which serves as a simple visualisation means for the computer-controlled positioning of a medical apparatus, such as the adjustment of the position and projection of a C-bow. Due to the reach of the laser beam, the operating surgeon may freely move in the operating theatre when indicating the straight line by means of the inventive device, so that it is possible, for example, to position the C-bow without getting in the way of the operating surgeon.

In the following, the invention and improvements of the invention will be illustrated in greater detail with reference to the partially diagrammatic representations of several embodiments.

IN THE DRAWINGS

Figure 2:
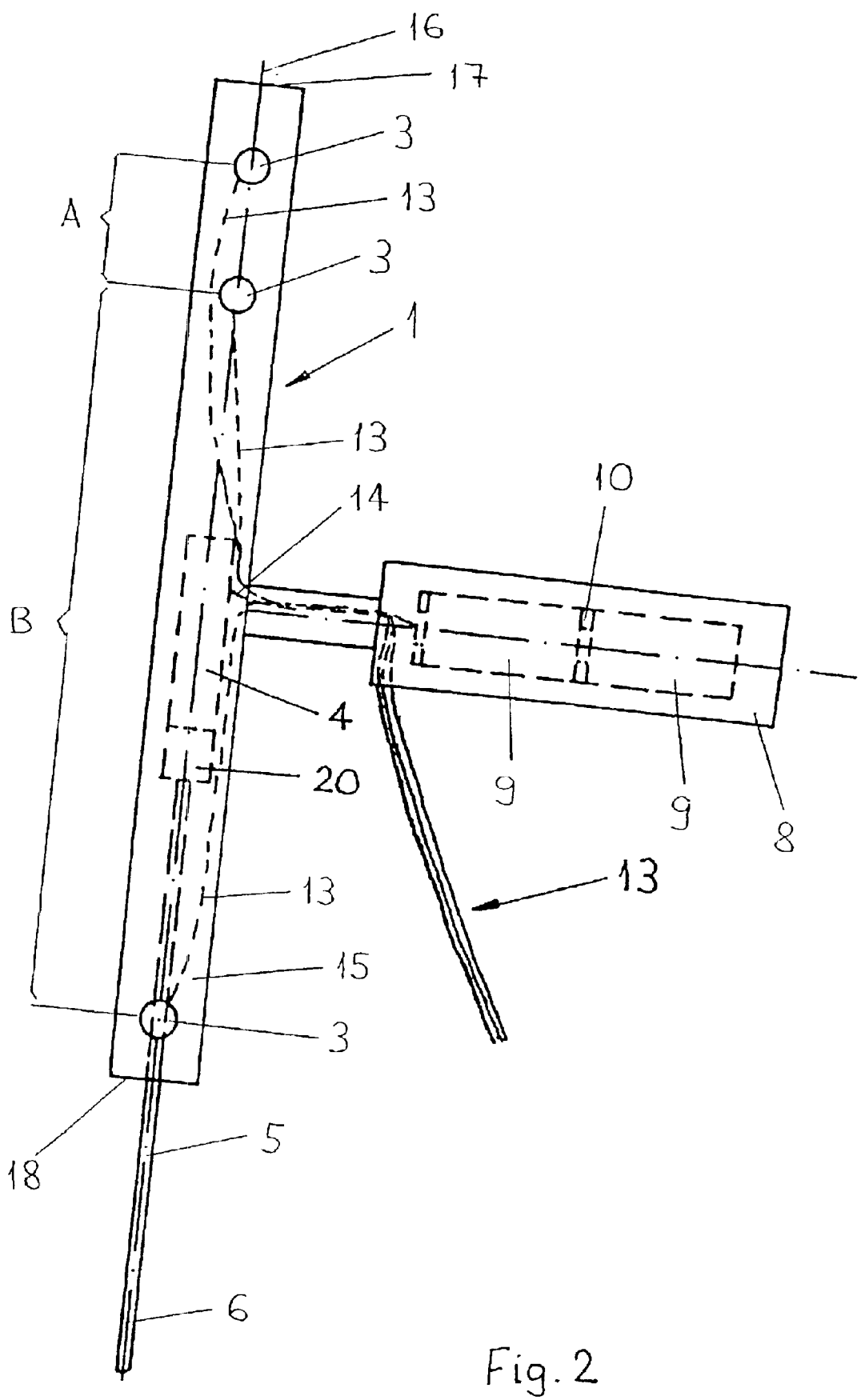

FIG. 1 is a perspective view of one embodiment of the device according to the invention; and FIG. 2 is a side view of another embodiment of the device according to the invention.

FIG. 1 shows an embodiment of the device according to the invention having a body 1 which is shaped in the form of a planar, triangular plate with a top surface 11 and a bottom surface 12, and a laser 4 which is arranged on centre relative to the ground plan of the plate and emits the laser beam 5 away from the bottom surface 12 into the operating theatre. The emitted laser beam 5 has a wave length in the visible range and a geometrical central axis 6. In order to allow the laser beam 5 to be emitted in a geometrically defined position and direction in relation to the markers 3, the laser 4 comprises means 20, preferably realisable in the form of a system of lenses, which are arranged in the area of the bottom surface 12 on the front portion of the laser 4. The body 1 is equally provided with three markers 3 embodied as LEDs placed each in one of the corners of the ground plan of the plate in such a way that the waves 19 embodied in the form of electromagnetic waves are emitted away from the top surface 11 into the operating theatre. A handle 8 is fixed on the side of the plate by means of which the body 1 is manually freely movable. The handle 8 comprises a cavity 10 wherein two batteries 9 serving as a source of energy for the laser 4 are accommodated. The power supply of the laser 4 is realised via a cable 14 which leads from the batteries 9 to the laser 4 and is integrated into the body 1. It would also be possible to pass the cable 14 on the outside of the body 1, either along the bottom surface 12 or along the top surface 11. The cables 13, which assure the power supply of the markers 3, are integrated into the body 1 on part of their lengths. The markers 3, embodied as LEDs, are supplied in a centralised way by the navigation system. For this purpose, the markers 3 embodied as LEDs are controlled in pulsed mode by the navigation system. The temporal correlation between the control pulses and the lighting up of the individual markers 3 enables the positional detection by the navigation system of the surgical instruments provided with markers 3 in the operating theatre.

The embodiment of the inventive device shown in FIG. 2 differs from the embodiment shown in FIG. 1 only in so far as the body 1 is shaped in the form of a cylindrical or prismatic rod 15. The rod 15 has a central axis 16, a front end portion 18, and a rear end portion 17. The laser 4 is integrated into the rod 15 and extends coaxially to the central axis 16. The means 20 permitting the laser beam 5 to be emitted in a geometrically defined position and direction relative to the markers 3, which as in the above example are preferably realised in the form of a system of lenses, are arranged on the front portion of the laser 4 and extend in the direction of the front end portion 18, so that the geometrical central beam 6 of the laser beam 5 coincides with the central axis 16. The handle 8 with the cavity 10 for receiving two batteries 9 assuring the power supply of the laser 4 is arranged on the rod 15 at a right angle to the central axis 16. The power supply of the laser 4 is realised via the cable 14 which is integrated into the rod 15 and connects the laser 4 to the batteries 9. Three markers 3, embodied, as in the above example, in the form of LEDs, are arranged on a straight line coinciding with the central axis 16, one marker 3 being arranged close to the front end portion 18, another marker 3 close to the rear end portion 17, and the third marker 3 being located in an intermediate position on the rod 15. The intermediate marker 3 and the marker 3 arranged close to the rear end portion 17 are separated by a distance A, whereas the intermediate marker 3 and the marker 3 arranged close to the front end portion 18 are separated by a distance B. The distances A and B are of unequal length (A<B) so as to make it possible to determine the direction of emission of the laser beam 5 from the measurement of the positions of the markers 3 by the navigation system. As in the above example, the cables 13, which assure the power supply of the markers 3, are integrated into the body 1 on part of their lengths and lead away from the handle 8 towards the navigation system.

What is claimed is:

1. A device to be used in combination with a surgical navigation system for defining the position of a straight line determined by an operating surgeon within a three-dimensional coordinate system in an operating theatre, including:
   A) a body (1) having a surface (2) and at least three markers (3) emitting waves (19), positions of said markers being determined within the three-dimensional coordinate system by means of a position detector that is part of the surgical navigation system; whereby
   B) the body (1) comprises a laser (4) that emits a laser beam (5), directed away from the body (1), said laser beam having a geometrical central beam (6) and a wavelength in the visible range; and
   C) a position of the central beam (6) relative to the three-dimensional coordinate system may be calculated from the determined positions of the markers (3) by means of a computer that is also part of the surgical navigation system; and wherein
   D) the body (1) is a planar plate with a top surface (11) and a bottom surface (12);
   E) the laser beam (5) is emitted so as to be directed away from the bottom surface (12); and
   F) the markers (3) are arranged in a plane extending parallel to the top surface (11) and the laser beam (5) is emitted vertically relative to said plane.

2. The device as claimed in claim 1, wherein the laser (4) comprises means (20) permitting the laser beam (5) to be emitted in a geometrically defined position and direction relative to the markers (3).

3. The device as claimed in claim 2, wherein said means (20) comprise a system of lenses adapted to the wavelength of the laser beam (5).

4. The device as claimed in claim 2, wherein the means (20) comprise a fiber-optic appliance permitting the laser beam (5) to be emitted in a geometrically defined position and direction relative to the markers (3).

5. The device as claimed in claim 1, wherein the body (1) comprises a handle (8).

6. The device as claimed in claim 1, wherein the laser (4) may be operated by at least one battery (9).

7. The device as claimed in claim 6, wherein the body (1) comprises a handle (8) and the handle (8) comprises a cavity (10) into which the at least one battery (9) is insertable.

8. The device as claimed in claim 1, wherein the laser (4) has a power range of between 2 mw and 1W.

9. The device as claimed in claim 8, wherein the laser power is between 2 mw and 25 mw.

10. The device as claimed in claim 1, wherein the waves (19) are electromagnetic waves.

11. The device as claimed in claim 10, wherein the markers (3) are light emitting diodes.

12. The device as claimed in claim 10, wherein the markers (3) are infrared light-emitting diodes.

13. The device as claimed in claim 10, wherein the markers (3) are optical reflectors.

14. The device as claimed in claim 10, wherein the markers (3) are fiber-optic light guides charged by a light source.

15. The device as claimed in claim 1, wherein the waves (19) are acoustic waves.

16. The device as claimed in claim 15, wherein the markers (3) are acoustic emitters.

17. The device as claimed in claim 1, wherein the body (1) is a planar plate having a longitudinal axis (16), a front end portion (18), and a rear end portion (17), and wherein the laser (4) is integrated into the planar plate so that the laser beam (5A) is emitted coaxially to the central axis (16) and directed away from either one of said front and rear end portions (17; 18).

18. The device as claimed in claim 1, wherein the at least three markers (3) are arranged on a straight line, a first two of said at least three markers (3) being separated from each other by a distance (A) and a second two of said at least three markers (3) being separated by a distance (B), the distances (A) and (B) being unequal.

19. The device as claimed in claim 18, wherein the straight line coincides with the central beam (6).

20. The device as claimed in claim 1, wherein, said at least three markers (3) are arranged in a non-collinear manner and emit waves from the body top surface (11), and the laser (4) is inserted substantially on center in the plate.

21. The device as claimed in claim 20, wherein said plane is formed by the top surface.

* * * * *